US007788043B2

(12) United States Patent
Gill et al.

(10) Patent No.: US 7,788,043 B2
(45) Date of Patent: Aug. 31, 2010

(54) METHODS, SOFTWARE ARRANGEMENTS AND SYSTEMS FOR ALIGNING SEQUENCES WHICH UTILIZES NON-AFFINE GAP PENALTY PROCEDURE

(75) Inventors: Ofer Gill, Springfield, NJ (US); Yi Zhou, Shanghai (CN); Bhubaneswar Mishra, Great Neck, NY (US)

(73) Assignee: New York University, New York, NY (US)

( * ) Notice: Subject to any disclaimer, the term of this patent is extended or adjusted under 35 U.S.C. 154(b) by 995 days.

(21) Appl. No.: 11/300,749

(22) Filed: Dec. 14, 2005

(65) Prior Publication Data

US 2006/0173631 A1 Aug. 3, 2006

Related U.S. Application Data

(60) Provisional application No. 60/636,410, filed on Dec. 14, 2004.

(51) Int. Cl.
*G06F 19/00* (2006.01)
*G06F 15/00* (2006.01)
*G11C 17/00* (2006.01)
(52) U.S. Cl. ................................. 702/20; 365/94; 700/1
(58) Field of Classification Search ........................ None
See application file for complete search history.

(56) References Cited

OTHER PUBLICATIONS

Mott Local sequence alignments with monotonic gap penalties Bioinformatics vol. 15, pp. 455-462 (1999).*
Waterman et al. Parametric sequence comparisons Proceedings of the National Academy of Sciences USA vol. 89, pp. 6090-6093 (1992).*
Kent et al. Evolution's cauldron: Duplication, deletion, and rearrangement in the mouse and human genomes. Proceedings of the National Academy of Sciences USA vol. 100, pp. 11484-11489 (2003).*
Altschul, S.F. et al., "Issues in Searching Molecular Sequence Databases." Nature Genetics, 1994, 6:119-128.
Altschul et al., "Basic Local Alignment Search Tool." Journal of Molecular Biology, 1990, 215: 403-410.
Brudno, M. et al., "LAGAN and Multi-LAGAN: efficient tools for large-scale multiple alignment of genomic DNA," Genome Research, Apr. 2003, 13(4):721-31.
Karlin, S. et al., "Methods for assessing the statistical significance of molecular sequence features by using general scoring schemes" Proc. Natl. Acad. Sci. USA, Mar. 1990, 87:2264-2268.
Karlin, S. et al., "Applications and statistics for multiple high-scoring segments in molecular sequences" Proc. Natl. Acad. Sci. USA, Jun. 1993, 90:5873-5877.
Lipman, D.J. et al., "A Tool for Multiple Sequence Alignment." Proceedings of the National Academy of Sciences USA, 1989, 86:4412-4415.
Miller, W. et al., "Sequence Comparison with Concave Weighting Functions" Bulletin of Mathematical Biology, 1988, 50:97-120.

Eugene W. Myers et al., "Optimal Alignments in Linear Space" CABIOS,1988, 4:1-13.
Needleman, S.B. et al., "A General Method Applicable to the Search for Similarities in the Amino Acid Sequences of Two Proteins." Journal of Molecular Biology, 1970, 48: 443-453.
Ophir, R. et al., "Patterns and rates of indel evolution in processed pseudogenes from humans and murids." Gene., 205(1-2) : Dec. 31, 1997, 191-202.
Pearson, W.R., "Comparison of Methods for Searching Protein Sequence Databases" Protein Science, 1995, 4:1145-1160.
Rice, P. et al., "EMBOSS: the European Molecular Biology Open Software Suite" Trends Genetics, Jun. 2000, 16(6) :276-7.
Smith, T.F. et al., "Identification of Common Molecular Subsequences." Journal of Molecular Biology, 1981, 147: 195-197.
Shpaer, E. et al., "Sensitivity and Selectivity in Protein Similarity Searches: A Comparison of Smith-Waterman in Hardware to BLAST and FASTA." Genomics. 1996. 38: 179-191.
Waterman, M.S. et al., "A New Algorithm for Best Subsequence Alignments with Applications to tRNA-rRNA Comparisons." Journal of Molecular Biology, 1987, 197: 723-728.
Zhang, Z. et al., "Patterns of nucleotide substitution, insertion and deletion in the human genome inferred from pseudogenes." Nucleic Acids Res., Sep. 15, 2003, 31(18) : 5338-48.
Xun Gu et al., "The Size Distribution of Insertions and Deletions in Human and Rodent Pseudogenes Suggests the Logarithmic Gap Penalty for Sequence Alignment" Journal of Molecular, 1995, pp. 464-473.
William H. Press et al., "Downhill Simplex Method in Multidimensions" Numerical Recipes: The Art of Scientific Computing, 1986, pp. 289-293.

(Continued)

*Primary Examiner*—John S Brusca
(74) *Attorney, Agent, or Firm*—Dorsey & Whitney LLP (57) ABSTRACT

Methods, software arrangements and systems are provided which can utilize an exemplary embodiment of a procedure which can enable an efficient alignment of DNA sequences using piecewise-linear gap penalties that closely approximate general and biologically meaningful gap-functions. Accordingly, an exemplary process, software arrangement and system can be provided for obtaining data associated with an alignment between at least two data strings having a plurality of positions in the data strings. For example, at least one characteristic of an alignment can be provided between the data strings using a particular function. The particular function is capable of evaluating gaps between the strings in the alignment based on a non-affine gap-penalty function. According to another exemplary embodiment of the present invention provides process, software arrangement and system for obtaining data associated with an alignment between at least two data strings having a plurality of positions in the data strings. In particular, the alignment which is approximately optimal in substantially all circumstance can be determined for a computation time that is proportional to products of lengths of the strings. For example, the alignment may be determined using space that is proportional to a sum of the lengths of the data strings.

38 Claims, 2 Drawing Sheets

OTHER PUBLICATIONS

William R. Pearson "Searching Protein Sequence Libraries: Comparison of the Sensitivity and Selectivity of the Smith-Waterman and FASTA Algorithms", Genomics 11, 1991, pp. 635-650.

Miller, W. et al., "Optimal Alignments in Linear Space" *CABIOS*, 4:11-17, 1988.

Hromkovic, J., "Heuristics." *Algorithms for Hard Problems, Second Edition*, 6:439-467, 2003.

Huang, X. et al., CABIOS vol. 6, No. 4, pp. 373-381 (1990).

* cited by examiner

METHODS, SOFTWARE ARRANGEMENTS AND SYSTEMS FOR ALIGNING SEQUENCES WHICH UTILIZES NON-AFFINE GAP PENALTY PROCEDURE

CROSS-REFERENCE TO RELATED APPLICATION(S)

This application is based upon and claims the benefit of priority from U.S. Patent Application Ser. No. 60/636,410, filed Dec. 14, 2004, the entire disclosure of which is incorporated herein by reference.

FIELD OF THE INVENTION

The present invention relates to methods, software arrangements and systems for comparative alignment of string sequence data, which in various embodiments is particularly useful aligning DNA or protein data.

BACKGROUND INFORMATION

Since biological sequences like DNA, RNA, and amino acid sequences, did not arise ab initio, but share a common ancestry and similar selection constraints. Thus, ultimately, elements may be conserved, motifs can be repeated, regions can be hyper-mutated or deleted, and segments can be inserted and reinserted over and over. A key focus in bioinformatics has been to enhance the ability to compare large number of these sequences against each other. This process can start with aligning two or more sequences using an algorithm that optimizes an alignment score, and often ends with organizing a set of sequences in a global tree structure where the tree-distances roughly correspond to the evolutionary distances. Both the score and distance functions can be determined by the underlying stochastic processes modeling genome evolution, and should be represented in a flexible manner in order to be faithful to biology. However, this type of generality can often imply a loss of computational efficiency. Such dilemma can be resolved through a reliance on simple algorithms, quasi-local cost functions (e.g., linear gap penalty), and by applying these algorithms preferably only on short subsequences after most unlikely candidates have been discarded.

To a rough approximation, a DNA sequence alignment problem differs marginally from a protein sequence alignment problem. For example, at a superficial level, DNA alignment is over an alphabet of 4 letters whereas protein alignment is over an alphabet of 20 letters. However, two key differences are that (1) there are 3 bp DNA code per amino acid, and (2) genes in DNA sequences that ultimately become transcribed and translated into proteins can be separated by intergenic regions of few thousands of base pairs that do not get expressed, and possibly, are subject to strikingly different (or no) selection constraints. Thus, these intergenic regions can typically vary to a greater extent in one species compared to another. Therefore, it is possible to expect gap lengths in DNA alignments to be larger, more variable, and have specie-specific distributions. Moreover, these distributions characterizing the gap-lengths may not be memory-less (i.e., may not follow exponential distributions). Thus, the traditional affine (or linear) gap functions used for aligning proteins may be unsatisfactory for DNA sequences, as the ultimate results can be biologically misleading.

SUMMARY OF THE INVENTION

Exemplary embodiments of methods, software arrangements and systems according to the present invention described herein are, e.g., based in part on recognizing that a non-exponential (e.g., power-law) distributions may be more appropriate than the ones leading to traditional affine gap functions for aligning sequences in general, and DNA sequences in particular. The evolutionary processes governing the genomes of species and the log-likelihood of certain indel gaps occurring when comparing one species against another indicate that a logarithmic gap function can be more appropriate for DNA sequences.

In order to exploit the fidelity of general non-linear gap functions for DNA sequences, without suffering performance penalties associated with them, exemplary methods, software arrangements and systems can be provided that can use piece-wise-linear gap functions modeled to approximate the gap functions in a dynamic programming approach. In one exemplary embodiment of the present invention, an alignment procedure can be used, herein designated as "PLAINS", that can use an optimal amount of storage (e.g., memory, hard drive, CD-ROM, etc.), avoids a major shortcoming associated with generalized gap penalties, and demands only a loss of constant factor (of $\leq 5.6$) in time complexity compared to the best algorithm using an affine-gap model. In comparison to other procedures that also proposed the piece-wise linear gap model (see Miller, W. et al., "Sequence Comparison with Concave Weighting Functions" *Bulletin of Mathematical Biology*, 50:97-120, 1988), an exemplary embodiment of the present invention can include several additional innovations in terms of worst-case upper-bound memory usage, alignment optimization, and visualization of data. In a further exemplary embodiment of the present invention, the exemplary PLAINS procedure can be provided in a bioinformatic environment, for instance in one such as "Valis". The exemplary embodiment can use a learning-heuristic to determine the best score function, a near-optimal gap-penalty model, and a scheme to determine p-values for reporting alignment reliabilities.

For example, the exemplary PLAINS procedure can operate on DNA sequences, and may be able to provide the underlying biological significances better than other existing procedures (e.g., needle, swat, emboss, etc.). As an example, alignment results for the genomic sequences of a pair of orthologous genes in Human and Fugu can be provided. While other alternative alignment procedures either possibly fail by mis-aligning the exons in the Fugu sequence, and/or by failing to identify important correlations, the exemplary embodiment of the "PLAINS" procedure according to the present invention is able to recover the orthologous relation between exons in the Fugu and Human sequences with good reliability.

The exemplary description of the exemplary embodiment is provided as follows. It first introduces the notations used throughout this document, overviews how the exemplary PLAINS procedure aligns, and describes how the exemplary PLAINS procedure performs its "logarithmic function to piecewise-linear function" approximation, alignment scoring, alignment reliability computations, parameter optimization, and color grid visualization scheme. Next, it describes the empirical results found from comparing the exemplary PLAINS procedure to other related procedures, and overviews the usage of PLAINS procedure. Finally, it concludes with a discussion of potential extensions and modifications for PLAINS procedure. The appendix section provides specific sequences used for the tests ran on PLAINS procedure as compared against similar alignment engines, as well as describes the exemplary embodiment of a PLAINS procedure alignment, including exemplary proofs of its space-bound and correctness.

The exemplary embodiment of the exemplary PLAINS procedure according to the present invention can use only linear space (e.g., in the worst case), and may obtain an alignment that is biologically most meaningful in spite of storage constraints. The alignment using the exemplary embodiment of the exemplary PLAINS procedure can be based on particular segment pairs from which it can learn optimized gap parameters based on interspecies alignments, and thus, identify more significant correlations in comparison to other procedures. The exemplary embodiment of the exemplary PLAINS procedure according to the present invention can be incorporated in a multi-scripting environment that includes intuitive visualization interfaces so as to allow users to view the alignments with a multiple-scale color grid scheme.

Provided herein is an exemplary software arrangement for obtaining data associated with an alignment between at least two data strings having a plurality of positions in the data strings. Such exemplary software arrangement can include a set of instructions, which when executed by a processing arrangement, are capable of controlling the processing arrangement to determine at least one characteristic of an alignment between the data strings using a particular function. The particular function can be capable of evaluating gaps between the strings in the alignment based on a piecewise linear non-affine gap-penalty function, for example.

Also provided herein is an exemplary system for obtaining data associated with an alignment between at least two data strings having a plurality of positions in the data strings. Such exemplary system can include a processing arrangement which is configured to determine at least one characteristic of an alignment between the data strings using a particular function. The particular function can be capable of evaluating gaps between the strings in the alignment based on a piecewise linear non-affine gap-penalty function, for example.

These and other objects, features and advantages of the present invention will become apparent upon reading the following detailed description of embodiments of the invention, when taken in conjunction with the appended claims.

The exemplary embodiments of the present invention can be related to one or more of the following publications, the entire disclosures of which are incorporated herein by reference in their entireties.

Altschul, S. F. et al., "Issues in Searching Molecular Sequence Databases." *Nature Genetics*, 6:119-128, 1994.

Brudno, M. et al., "LAGAN and Multi-LAGAN: efficient tools for large-scale multiple alignment of genomic DNA," *Genome Research*, 13(4):721-31, April 2003.

Nevill-Manning, C. G. et al., "Pairwise protein sequence alignment using Needleman-Wunsch and Smith-Waterman algorithms," Personal communication (http://motif.stanford.edu/alion/), 1997.

Gu X, Li W H., "The size distribution of insertions and deletions in human and rodent pseudogenes suggests the logarithmic gap penalty for sequence alignment." *J Mol Evol.*, 40(4):464-73, April 1995.

Hromkovic, J., "Heuristics." *Algorithms for Hard Problems, Second Edition*, 6:439-467, 2003.

Huang, X. et al., *Advanced Applied Mathematics*, 12:373-381, 1991.

Karlin, S. et al., "Methods for assessing the statistical significance of molecular sequence features by using general scoring schemes" *Proc. Natl. Acad. Sci. USA*, 87:2264-2268, March 1990.

Karlin, S. et al., "Applications and statistics for multiple high-scoring segments in molecular sequences" *Proc. Natl. Acad. Sci. USA*, 90:5873-5877, June 1993.

Lipman, D. J. et al., "A Tool for Multiple Sequence Alignment." *Proceedings of the National Academy of Sciences USA*, 86:4412-4415, 1989.

Miller, W. et al., "Sequence Comparison with Concave Weighting Functions" *Bulletin of Mathematical Biology*, 50:97-120, 1988.

Miller, W. et al., "Optimal Alignments in Linear Space" *CABIOS*, 4:11-17, 1988.

Needleman, S. B. et al., "A General Method Applicable to the Search for Similarities in the Amino Acid Sequences of Two Proteins." *Journal of Molecular Biology*, 48: 443-453, 1970.

Ophir, R. et al., "Patterns and rates of indel evolution in processed pseudogenes from humans and murids." *Gene.*, 205(1-2): 191-202, 1997 Dec. 31.

Pearson, W. R., "Comparison of Methods for Searching Protein Sequence Databases." *Protein Science*, 4:1145-1160, 1995.

Pearson, W. R., "Searching Protein Sequence Libraries: Comparison of the Sensitivity and Selectivity of the Smith Waterman and FASTA algorithms." *Genomics*, 11: 635-650, 1991.

Press, W. H. et al., "Downhill Simplex Method in Multidimensions." *Numerical Recipes: The Art of Scientific Computing*, 10.4: 289-293, 1986.

Rice, P. et al., "EMBOSS: the European Molecular Biology Open Software Suite" *Trends Genetics*, June 16(6):276-7, 2000.

Smith, T. F. et al., "Identification of Common Molecular Subsequences." *Journal of Molecular Biology*, 147: 195-197, 1981.

Shpaer, E. et al., "Sensitivity and Selectivity in Protein Similarity Searches: A Comparison of Smith-Waterman in Hardware to BLAST and FASTA." *Genomics*, 38: 179-191, 1996.

States, D. J. et al., "Basic Local Alignment Search Tool." *Journal of Molecular Biology*, 215: 403-410, 1990.

Waterman, M. S. et al., "A New Algorithm for Best Subsequence Alignments with Applications to tRNA-rRNA Comparisons." *Journal of Molecular Biology*, 197: 723-728, 1987.

Zhang, Z. et al., "Patterns of nucleotide substitution, insertion and deletion in the human genome inferred from pseudogenes." *Nucleic Acids Res.*, 31(18): 5338-48, 2003 Sep. 15.

BRIEF DESCRIPTION OF THE DRAWINGS

Further objects, features and advantages of the invention will become apparent from the following detailed description taken in conjunction with the accompanying figures showing illustrative embodiments of the invention, in which.

DETAILED DESCRIPTION

Exemplary Plains Alignment Procedure

For the purpose of this description, it should be assumed that the two strings to be aligned are denoted X and Y, and their respective lengths are m and n. Also, it should be assumed that the penalty for each mismatch is denoted as ms. (Note, X and Y should not be confused with x and y, as the capital letters denote strings and the small letters, positions within such strings).

Next, a p-part piecewise-linear function can be denoted as $ww(\cdot)$. This function has a y-intercept of wo, and the slopes of the linear functions in successive intervals are $wc_1, wc_2, \ldots, wc_p$, and the x-values at which one interval ends and the next begins are denoted $k_1, k_2, \ldots, k_{p-1}$, and $k_u$ is the x-value where the $u_{th}$ linear function of slope $wc_u$ ends. Also, should be assumed that $k_0=0$, and that the $p_{th}$ function of slope $wc_p$ never ends (i.e., extends off into infinity). Then, for some value i such that $k_{p-1} < i \leq k_p$, ww(i) is defined as:

$$ww(i) = wo + [wc_{\bar{p}}(i - k_{\bar{p}-1})] + \sum_{u=1}^{\bar{p}-1}[wc_u(k_u - k_{u-1})].$$

For all practical and/or exemplary purposes, it is sufficient to set p to be at most 10. With the mismatch penalty ms and the piecewise-linear gap penalty function $ww(\cdot)$, and reward per match fixed at 1, the exemplary PLAINS procedure according to the present invention can generate an alignment technique, similar to that described in Miller, W. et al., "Sequence Comparison with Concave Weighting Functions" *Bulletin of Mathematical Biology*, 50:97-120, 1988. However, because the exemplary embodiment of the exemplary PLAINS procedure according to the present invention can exclusively use piecewise-linear gap functions (as opposed to general gap functions), it is capable of taking advantage of its very own technique, and can work with only O(np) space in the worst-case. For practical and/or exemplary purposes, $p \leq 20$, the exemplary PLAINS procedure according to the present invention can use worst-case linear space. Further details of how the exemplary PLAINS procedure can generate an alignment, and exemplary proofs of its O(np) space bound and the correctness of the computed alignment obtained are explained in appendices B, C, and D herein.

For example, n=length of the second sequence, p=the number of parts used in the given piecewise-linear gap function (e.g., the exemplary PLAINS Procedure may allow p to be only at most 10). O(n) is an algorithmic notation used for describing asymptotic computational complexity by a function bounded by at most a constant k times n, where k may be considered too unimportant to be explicitly estimated. The memory space utilized by the exemplary PLAINS Procedure is O(np), e.g., the space used by the exemplary PLAINS Procedure is at most k*n*p (e.g., k can be approximately 2). This can be called a "linear" space because the exemplary PLAINS Procedure can set p to be at most 10, and hence the worst-case memory usage is only linear in terms of n.

Summary of Execution of Exemplary Plains Procedure

Figure 4:
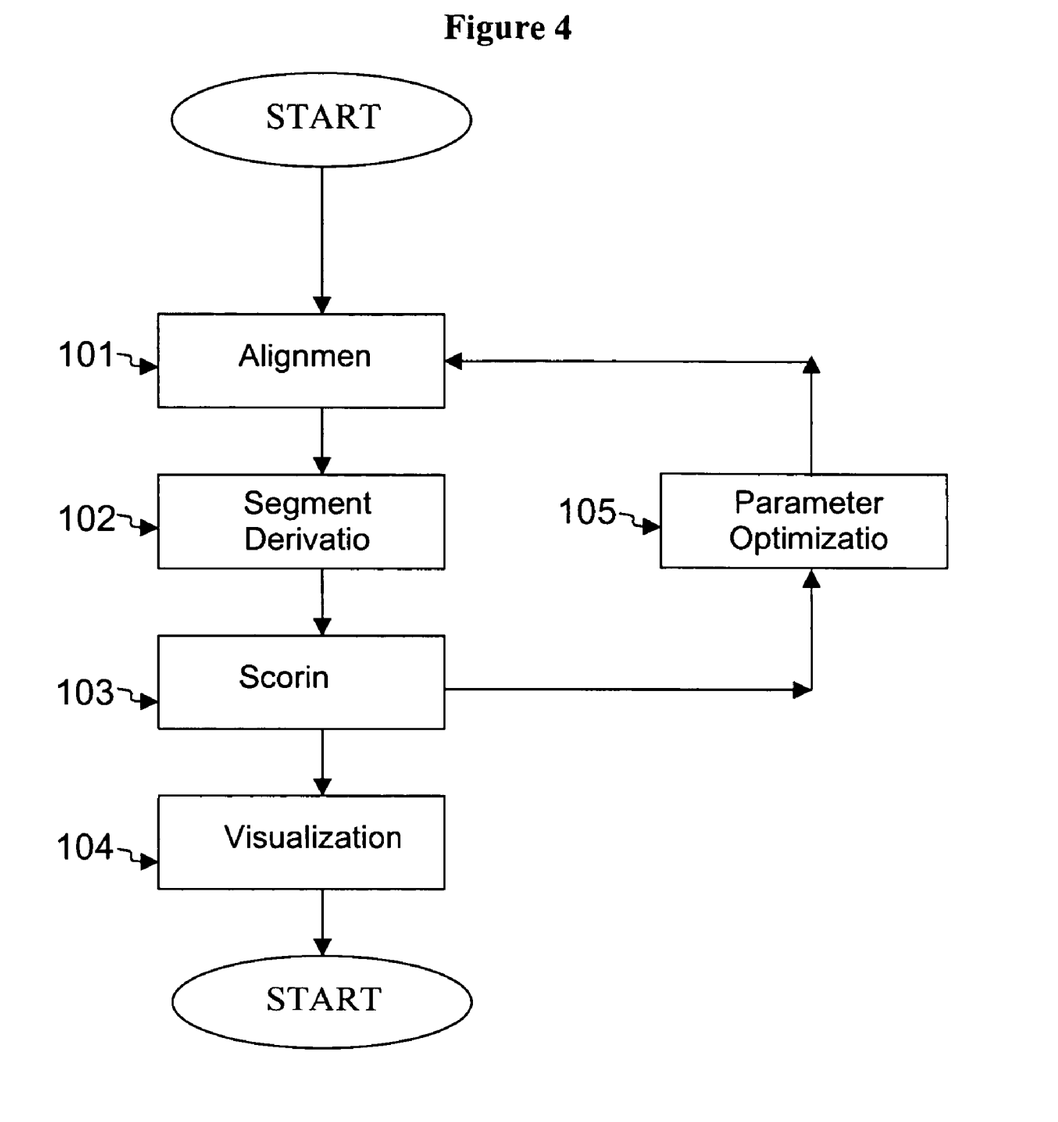
FIG. 4 is a flow diagram of an exemplary embodiment of the exemplary PLAINS procedure in accordance with the present invention.

Provided below is a brief description of the operation of an exemplary embodiment of the exemplary PLAINS procedure according to the present invention, the high level flow diagram of which is shown in FIG. 4.

(1) For example, for a set of gap/mismatch parameters, an alignment can be performed using a dynamic programming table in linear space, using a technique which can be the same as or similar to as those described in the Miller-Myers publication (See FIG. 4, step 101). This exemplary technique can execute the alignment one or more times, recording alignment information at different locations of the dynamic-programming (DP) table each time. These alignment information pieces are associated to make the overall alignment. This step is approximately identical to that of the Miller-Meyers procedure, except that only piecewise-linear gap formulas are utilized, and can be furnished with a proof as to why only linear amount of space is used in the worst case, while still being able to obtain the same alignment obtainable in quadratic space.

(2) When this alignment is obtained, certain (e.g., important) segments can be derived therefrom based on areas of highest match percentages. (See FIG. 4, step 102). For example, it is possible to locate the Karlin-Altschul coincidental probabilities of these segments, and remove those that are unreliable.

(3) Based on the segments that are maintained, a score R can be provided therefore, and a zeta may be determined (see FIG. 4, step 103), with the Karlin-Altschul joint coincidental probability over all the segments being maintained, as well as zeta'=−log(zeta). The results for this step are provided for the exemplary PLAINS, EMBOSS, LALIGN, and LAGAN Procedures in tables 1 through 4.

Figure 2:
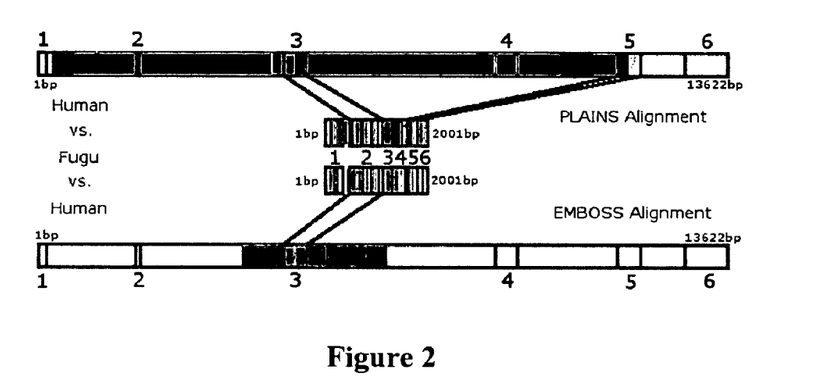
FIG. 2 is an illustration of Match Ratio Color Lines in an HF Ortho2 test utilized by an exemplary embodiment of the exemplary PLAINS procedure in accordance with the present invention as compared to a conventional EMBOSS method.
Figure 3:
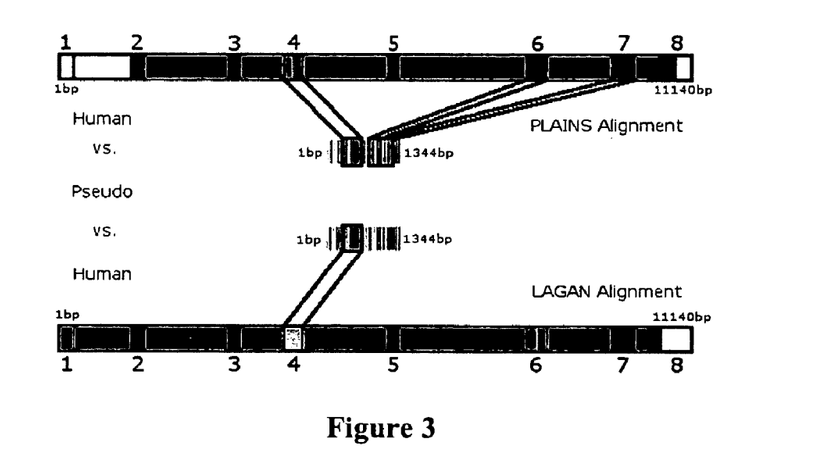
FIG. 3 is an illustration of Match Ratio Color Lines in the HumanPseudo5 test usable by an exemplary embodiment of the exemplary PLAINS procedure according to the present invention as compared to a LAGAN procedure.

(4) Also based on computed alignment, it is possible to visualize that alignment using a Color grid to highlight all the high and low match areas. (See FIG. 4, step 104). Results for this step are shown for the exemplary PLAINS Procedure versus the EMBOSS Procedure and the exemplary PLAINS Procedure versus the LAGAN Procedure in FIGS. 2 and 3, respectively, using two specific exemplary experiments. For example, FIG. 2 illustrates Match Ratio Color Lines in an HF (Human-Fugu) Ortho2 test for the exemplary PLAINS procedure in comparisons to the conventional EMBOSS method, with the Human and Fugu sequence used including six exon regions that correspond to each other (though not necessarily in order, as exon region 2 in the Fugu sequence corresponds to exon region 3 in Human sequences for example) and both the exemplary PLAINS and EMBOSS procedures correctly identifying the correlation of exon region 2 in Fugu with exon region 3 in Human, but only the exemplary PLAINS procedure identifies the correlation of exon region 5 in Fugu with exon region 5 in Human. FIG. 3 illustrates Match Ratio Color Lines in the HumanPseudo5 test for the exemplary PLAINS procedure in comparison to the LAGAN procedure, the Human sequence having 8 exon regions that are similar to areas of the pseudosequence used, and although alignments of the exemplary PLAINS and LAGAN procedures for these cases are similar, even by a peripheral review of the ColorGrids, the exemplary PLAINS Procedure is more sensitive in detecting significance, and thus the exemplary PLAINS and LAGAN procedures both identify exon region 4 as important, but the exemplary PLAINS procedure also deems exon regions 6 and 7 in the Human sequence as important, which LAGAN misses.

Figure 1:
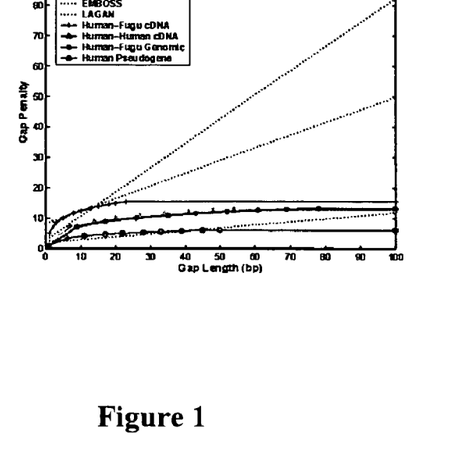
FIG. 1 is an illustration of Piecewise-Linear Gap Functions which can be generated using an exemplary embodiment of the exemplary PLAINS procedure according to the present invention.

(5) The exemplary embodiment of the exemplary PLAINS procedure according to the present invention can optimize gap and mismatch parameters based on the scores described in procedure paragraph (3) above. This parameter-estimation can be performed by executing procedures (1)-(3) over different parameters, and maintain the set of parameters that give the best R score. (See FIG. 4, step 105). The exemplary PLAINS Procedure can use two techniques to optimize parameters, e.g., Simulated Annealing ("SA") and Genetic Algorithm ("GA"). Both SA and GA may have a defined way to test subsequent parameters based on the results of previous parameters. Furthermore, SA and GA can each execute steps (1)-(3) as a black-box over any particular set of parameters. When the best parameters are found, the alignment corresponding to those parameters can be visualized using step (4) if appropriate. The results of this step are shown in FIG. 1. For example, FIG. 1 illustrates Piecewise-Linear Gap Functions which can be generated using an exemplary embodiment of the exemplary PLAINS procedure according to the present invention in optimizing an R score for different species pairs, and rescaled gap-parameters from other conventional procedures such as LAGAN (LAGAN gap parameters shown are its default parameters, and LAGAN uses a number of unspecified gap parameters in aligning on a species by species basis).

For a known alignment, it is possible to execute procedures (2)-(4) alone. These steps do not require any knowledge of how the alignment was generated. This is how it is possible to compare LALIGN, LAGAN, and EMBOSS to PLAINS without needing to know how those tools work. Also, because the zeta' values for an alignment is more meaningful than the R score, it is possible to compare tools based on zeta', even though gap/mismatch parameters can be optimized using the exemplary PLAINS Procedure for step (5) based on the R score.

Plains Log Approximation and Parameter Optimization

Recall the definition for a p-part piecewise-linear gap function ww(•). For a given piecewise-linear gap function and mismatch penalty, the exemplary PLAINS Procedure does find the best alignment for X and Y. When a user asks the exemplary PLAINS Procedure to find the "best set" of gap-mismatch parameters that yield a "best alignment," the exemplary PLAINS Procedure optimizes over four variables: $\alpha$, $\beta$, d, and ms. The penalty for each mismatch is denoted ms, as in the previous section. If the gaps follow a power-law distribution, then the best gap penalty function, determined by the log-likelihood, follows a logarithmic gap function. It has been found that such gap functions give the best alignments. Since piecewise-linear functions can be modeled to resemble convex general functions (with some controllable degree of accuracy), the exemplary PLAINS optimization models piecewise-linear functions to approximate the continuous logarithmic function. In the extreme case, such a piecewise-linear function assumes an affine function (corresponding to an exponential distribution for gap lengths), and thus exemplary PLAINS procedure retains the generality for a wide class of distributions.

More specifically, the logarithmic gap penalty function over i is denoted as: $\alpha \ln(i+1)+\beta$. For a given d, $\alpha$, and $\beta$, ww(•) uses $k_1, \ldots, k_p$ values set to d, 2d, ..., p*d, and for each u from 0 to p, $ww(k_u)=\alpha \log(k_u+1)+\beta$, and from this, one can calculate the slope $wc_u$ for each uth line, and wo is set to $\beta$. Note: ln is $\log_e$ using base e, and ln(i+1) is used instead of ln(i), with the result that the function takes the value=$\beta$ for i=0. Also note that for the pth line, $wc_p$ is computed assuming that $k_p=p*d$, even though $k_p$ is later assumed to be infinity, and the pth line of the piecewise-linear function is assumed to continue off into infinity.

Computational exploration reveals that varying any of ms, $\alpha$, $\beta$, and d results in different alignments. Each alignment is given a score "adaptively" (i.e., the score given to each alignment is not the same score found in the dynamic programming table) in a way explained in the next section, and among this collection of alignments, the one with the highest score is considered "the best."

It is possible to view the gap/match-mismatch parameters ($\alpha$, $\beta$, d, ms) as a vector v, and its corresponding score as a scalar=f(v), where f can map each vector to its corresponding ratio score. Thus, for a given vector v', it is possible to determine f(v') by performing an alignment using parameters specified by v'. Hence, the problem the exemplary PLAINS procedure operates on becomes one of obtaining a vector v to maximize f(v), which is a numerical optimization problem.

As per user's request, the exemplary PLAINS procedure can locate v to optimize f(v) using Simulated Annealing and/or Genetic procedure. Both of these procedures are described in Hromkovic J, "Heuristics." *Algorithms for Hard Problems, Second Edition*, 6:439-467, 2003. Empirical runs using the exemplary PLAINS procedure have shown that Simulated Annealing provides better results, but Genetic procedure explores the space of v more thoroughly. However, this is likely because (1) Monte Carlo-related methods are successful in optimizing Hidden Markov Models (which are similar to sequence alignments), and (2) Genetic procedures typically consider subsequent solutions in a more random manner than Simulated Annealing. The exemplary PLAINS procedure can allow any other technique to optimize gap/match-mismatch parameters, instead of using these two optimization methods. For example, it is possible to search parameters with a somewhat time consuming MCMC approach, or variants such as Gibbs sampler or EM.

Plains Scoring System

For a fixed set of gap/match-mismatch parameters ($\alpha$, $\beta$, d, ms), the exemplary PLAINS procedure can create an alignment, and score it by obtaining segment pairs that yield "good" scores. The sum of these segment pairs' scores R may be the value that the exemplary PLAINS procedure reports, and not the score obtained from the dynamic programming table. This approach is sensible because when an alignment is observed, it is the segment pairs of high scores that are likely the true items of significance.

There are a number of ways to optimally select segment pairs. The method chosen by the exemplary PLAINS procedure uses a technique, which creates the alignment first, and uses the alignment to obtain the segment pairs. There is a simple reason why the exemplary PLAINS procedure uses a technique, which does not need to obtain the segment pairs from the dynamic programming table like most other procedures. It is because the exemplary PLAINS procedure can use linear space in a storage arrangement (e.g., memory), and obtain the segment pairs from the dynamic programming table would typically require quadratic space in some way or another. Furthermore, the exemplary PLAINS procedure can assume that both mismatches and gaps are allowed in the segment pairs (though sparingly, since the segment pair should be considered a "good" one).

Using fixed constants W, $\omega$, and $\rho$ (where W is an integer, and $\omega$ and $\rho$ are real numbers within [0, 1]), the exemplary embodiment of the exemplary PLAINS procedure according to the present invention can obtain the segment pairs from an alignment A of length a in following manner:

(1) For all i from 1 to a−(W−1), the exemplary PLAINS procedure can determine a pa(i) value, which is the percentage of entries in A[i ... i+W−1], where a match has occurred. It is then possible to determine μ and σ, the mean and standard deviation of the pa(•) values. Next, one mark any pa(•) values can be marked as "special" if they exceed μ+ωσ. The choice of using μ+ωσ as the cutoff value instead of a fixed constant provides the exemplary PLAINS procedure the flexibility to obtain the important regions in two sequences, regardless of how homologous they are to each other.

(2) For each u and u' (with u<=u'), if pa(u), pa(u+1), ... pa(u') are all marked as "special", but pa(u−1) and pa(u'+1) are not, then it is possible to produce a segment pair that ranges from A[u ... u'+W−1] (i.e., a segment pair that starts at the leftmost entry pa(u) represents, and ends at the rightmost entry that pa(u') represents).

(3) Each segment pair P can be trimmed so that it starts and ends at a position in the alignment where a match occurred. Next, it is possible to merge together any segment pairs that overlap (i.e., if a segment pair $P_1$ starts at position $u_1$ and ends at position $v_1$, and a segment pair $P_2$ starts at position $u_2$ and ends at position $v_2$, and $u_1 < u_2$, and $v_1 \geq u_2$, one merges the two segment pairs into a new segment pair P which begins at us and ends at max($v_1$, $v_2$).)

(4) With all segment pairs representing non-overlapping regions, it is possible to assign a score to each segment pair (i.e., if a segment pair P starts at position u and ends at position v, then one evaluates the score of subalignment A[u ... v] using the given gap/mismatch penalties ww and ms. For example, it is possible to give 1 point per match. All segment pairs kept at step (4) must begin and end at a point in the alignment where a match occurs.)

(5) For each score S given to each segment pair P, it is possible to determine the Karlin-Atschul probability $p=1-\exp(-Kmne^{-\lambda S})$ as described in Karlin S. et al., "Methods for assessing the statistical significance of molecular sequence features by using general scoring schemes", *Proc. Natl. Acad. Sci. USA*, 87:2264-2268, March 1990. Any segment pairs whose p>ρ, can be deleted since this may signify a segment pair that "occurs by chance," and does not represent a significant relation between X and Y. The choice of selection of K and λ values can be described later.

(6) The r segment pairs kept at this step are considered the "good" ones. One now computes R, the sum of the scores of the "good" segment pairs (i.e., if the ith "good" segment pair has score $S_i$, then one computes $$\left(R = \sum_{i=1}^{r} [S_i]\right).$$

It is also possible to determine ζ, the Karlin-Atschul probability for the r segments. If $S'_i = \lambda S_i - \ln(Kmn)$, and $T_r = S'_1 + ... + S'_r$, (as described in Karlin S, Altschul S. F., "Applications and statistics for multiple high-scoring segments in molecular sequences" *Proc. Natl. Acad. Sci. USA*, 90:5873-5877, June 1993), $$T_r = \sum_{i=1}^{r} [S'_i] = \sum_{i=1}^{r} [\lambda S_i - \ln(Kmn)] = \lambda \sum_{i=1}^{r} [S_i] - r\ln(Kmn) = \lambda R - r\ln(Kmn),$$

and $$\zeta = \mathrm{Prob}(T_r \geq x) \approx \frac{e^{-x} x^{r-1}}{r!(r-1)!}.$$

This value can act as an overall probability for the "good" segment pairs.

Setting W=50, ω=0.5, ρ=0.5 empirically yields segment pairs that are reasonably long, and have significantly higher matches than the alignment "background". With these values for W and ω, the exemplary PLAINS procedure was run on over 900 pairs of randomly generated sequences, each with lengths ranging from 500 through 4000, and the observed "good" segment pairs were tallied. (Step 5 was temporarily omitted for such runs, which is the step where one eliminates segment pairs based on the ρ values). From this empirical study, it was estimated that K=3.31*10^−4 and λ=0.0762.

Using the known K, λ, W, ω, ρ values, PLAINS can take any prespecified gap/mismatch parameters ms and ww, and report for sequences X and Y the overall alignment A obtained, along with all the "good" segment pairs, their scores and p values, and the R score and ζ value. In the event that r=0, then R=0 and the exemplary PLAINS procedure can indicate that no "good" segments were obtained.

Plains Color-Grid Technique

For visualization of the determined alignments, the exemplary embodiment of the exemplary PLAINS procedure ported in Valis can use a coloring grid to summarize high and low matched areas for X found in the alignment. It operates, e.g., as follows: For some M (different from N), the grid is colored with at most M spots. Color spot 1 was set based on the match percentage found in X[1, ..., m/M] in the alignment; color spot 2 was set to a color based on the match percentage found in X[m/M+1, ..., 2m/M] in the alignment; spot i was set to a color based on the match percentage found in X[(i−1) m/M+1, ..., im/M] in the alignment, and so on. The coloring grid for Y operates in a similar manner. FIGS. 2 and 3 are examples of this exemplary operation, with bright colors signifying high-match areas, and dark colors signifying low-match areas. White signifies any nucleotides of X or Y on the left/right sides that were unaligned.

The number of match percentages obtained has a fixed size. The color computations in this manner has a number of advantages, such as how it handles the limited resolution of the computer screen compared to the sizes of X and Y.

In addition to visualizing color grids for all of X and Y, it provides the option to view portions of X or Y by specifying a substring range for either X or Y, with the color grid of the unspecified sequence automatically resized to represent the corresponding area in the specified sequence's substring.

Empirical Results

Two sets of experiments were performed and used to compare the exemplary PLAINS procedure to other similar alignment procedures. The first set involved related sequences. The second set involved unrelated sequences. Tables 1 and 2 provide details regarding both sets of test runs, and Appendix A provides further information.

For example, the exemplary PLAINS procedure is compared against the similar localized DNA alignment tools of EMBOSS, LAGAN, and LALIGN procedures. The LAGAN procedure uses piecewise-linear gap functions similar to the exemplary PLAINS procedure, whereas the EMBOSS and LALIGN procedures use linear gap functions.

The exemplary PLAINS procedure optimizes the approximate best gap/mismatch parameters based on the pair of species aligned, and the nature of the sequence. For the runs using Human and Fugu sequences, the parameters where the LAGAN procedure provided the best results were used. The LAGAN procedure has special gap-parameters for Human and Mouse, but not Fugu. In contrast, the EMBOSS and LALIGN procedures each use a fixed set of gap/mismatch parameters for all species. FIG. 3 shows the piecewise-linear gap functions that the exemplary PLAINS procedure provides for each species pair. All gap parameters are normalized by dividing by the reward-per-match value of an alignment tool. This normalization is done in order to fairly compare one procedure with another. Also, for the same reason, all R scores reported herein are also normalized by dividing by a tool's reward-per-match value.

$\zeta'$ values obtained from each run (where $\zeta'=-\log(\zeta)$). As discussed above, r is the number of "good" segment pairs, R is the total score of all those segment pairs, and $\zeta$ is the probability of having the "good" segment pairs sum up to R. The $\zeta'$ values are displayed instead of the $\zeta$ values, because $\zeta'$ values are easier to compare. Note that more reliable alignments correspond to smaller $\zeta$ values, and hence, larger $\zeta'$ values. When no "good" segment pairs are found, an X is placed as the value. In the HFncd2 and HFncd3 experiments, an X is placed as the R, r, and $\zeta'$ values for the EMBOSS procedure because the EMBOSS procedure ran out of memory while aligning those experiments.

As these results show, the exemplary PLAINS procedure yielded the highest R and r values for the most part. However, because different alignment algorithms use different gap/mismatch parameters in different cases, it is actually the $\zeta'$ value which holds the most significance (e.g., with higher $\zeta'$ indicating that the alignment is less likely to happen "by chance"). Many of the genomic alignments yielded by the

TABLE 1

Sequence Descriptions for the Related Experiments Ran. All the sequences are retrieved from ENSEMBL database [www.ensembl.org]. Note for the rightmost column: (nt) indicates match percentage of nucleotides, (aa) indicates match percentage of animo acids after the two DNA sequences are transcribed into proteins.

| Name | Species | Lengths | Sequence Nature | Large Gaps? | Identity Percentage in Homologous Regions |
|---|---|---|---|---|---|
| humanHomol__15 | Human vs. | 8K vs. | coding | no | 86% (nt) |
| humanHomol__16 | Mouse | 400-3000 | | | 90% (nt) |
| MousePseudo1 | Mouse | 2.4K-9.6K | noncoding | yes | 62% (nt) |
| MousePseudo2 | vs. | vs. | | | 55% (nt) |
| MousePseudo3 | Pseudogene | 400-500 | | | 56% (nt) |
| HumanPseudo1 | Human | 1.5K-11.2K | noncoding | yes | 83% (nt) |
| HumanPseudo2 | vs. | vs. | | | 74% (nt) |
| HumanPseudo3 | Pseudogene | 400-4000 | | | 85% (nt) |
| HumanPseudo4 | | | | | 74% (nt) |
| HumanPseudo5 | | | | | 75% (nt) |
| HFugu2r | Human | 6K-12K | noncoding | yes | 58% (aa) |
| HFortho1 | vs. | vs. | | | 55% (aa) |
| HFortho2 | Fugu | 1.8K-3.6K | | | 52% (aa) |
| HFortho3 | | | | | 64% (aa) |
| HFortho4 | | | | | 52% (aa) |
| HFortho5 | | | | | 73% (aa) |

TABLE 2

Sequence Descriptions for the Unrelated Experiments Ran. All the sequences are retrieved from ENSEMBL database [www.ensembl.org].

| Name | Species | Lengths | Sequence Nature |
|---|---|---|---|
| HFncd1 | Human | 10K-20K | noncoding |
| HFncd2 | vs. | vs. | |
| HFncd3 | Fugu | 6K-10K | |
| FFcd1 | Human, Fugu, | 1.5K-4.8K | coding |
| HFcd1 | and Mouse | vs. | |
| HHcd1 | (All six combinations) | 1.5K-4.8K | |
| HMcd1 | | | |
| MFcd1 | | | |
| MMcd1 | | | |

All scores for all alignment techniques were obtained directly from the alignments and not the dynamic programming table, as described above in "PLAINS Scoring System" section. As shown in tables 3 and 4, respectively, the R, r, and four described procedures have caught exons in the alignment, but most of these exons caught are not included in the "good" regions of the alignment, because the Karlin-Atschul probability concluded that their results are unreliable. FIG. 3 shows an example of this phenomenon, since both the exemplary PLAINS and LAGAN procedures identify most of the exons in the human sequence, but only the exemplary PLAINS procedure counts the exons that the tools identify as lying within the "good" regions.

The MousePseudo (alignments of Mouse genes against corresponding pseudogenes), and humanHomol (alignment of Human genes against homologous Mouse genes) runs were, for the most part, a relatively close competition between the four alignment tools, in terms of actual alignments obtained, especially between the exemplary PLAINS and LAGAN procedures. This experimental result indicates either the inferiority of linear gap functions relative to piecewise-linear gap functions, or the inferiority of using general-case gap parameters relative to using customized gap parameters per species, or most likely, both.

For most of the HumanPseudo (alignments of Human genes against corresponding pseudogenes) runs, the exemplary PLAINS and LAGAN procedures yielded alignments with many similar correlations, but the results reported by PLAINS are more reliable (higher ζ' values). One illustration of this is FIG. 3, which compares the results of the exemplary PLAINS procedure to the LAGAN procedure for HumanPseudo5 in further detail. Furthermore, in HumanPseudo4, PLAINS was the technique that obtained any significant correlation.

However, an interesting results obtained were in the HFugu2r and HFortho runs, the runs involving genomic Human and Fugu sequences. Since the evolutionary distance between the human and fugu species is significantly long, even the most conserved exon regions of the orthologous gene in the two genomes are expected to have diverged quite a lot (despite the protein sequences still sharing high homology). Furthermore, the two genomes have different gene structures—the genes in the Fugu genome have very short introns, while the introns in the Human genome are usually very long.

TABLE 3

Related Run Scores for PLAINS, EMBOSS, LAGAN, and LALIGN.

| Test Name | PLAINS | | | EMBOSS | | | LAGAN | | | LALIGN | | |
|---|---|---|---|---|---|---|---|---|---|---|---|---|
| | R | r | ζ' | R | r | ζ' | R | r | ζ' | R | r | ζ' |
| humanHomo1_15 | 116.871 | 1 | 0.894 | 110.000 | 1 | 0.686 | 112.000 | 1 | 0.745 | 110.000 | 1 | 0.686 |
| humanHomo1_16 | 2184.956 | 1 | 68.343 | 1751.000 | 2 | 48.256 | 2064.917 | 1 | 64.370 | 1568.200 | 4 | 32.441 |
| MousePseudo1 | 267.956 | 2 | 3.168 | 265.200 | 2 | 3.087 | 268.000 | 2 | 3.169 | 166.000 | 1 | 2.965 |
| MousePseudo2 | 106.319 | 1 | 0.562 | 203.200 | 2 | 0.784 | 109.667 | 1 | 0.658 | 109.400 | 1 | 0.650 |
| MousePseudo3 | 0.000 | 0 | X | 0.000 | 0 | X | 0.000 | 0 | X | 0.000 | 0 | X |
| HumanPseudo1 | 281.992 | 3 | 1.881 | 255.200 | 3 | 1.437 | 83.250 | 1 | 0.470 | 84.400 | 1 | 0.502 |
| HumanPseudo2 | 281.851 | 3 | 1.372 | 0.000 | 0 | X | 89.000 | 1 | 0.332 | 0.000 | 0 | X |
| HumanPseudo3 | 1782.646 | 8 | 21.827 | 1066.700 | 5 | 11.998 | 1383.583 | 8 | 16.858 | 439.200 | 2 | 5.415 |
| HumanPseudo4 | 110.620 | 1 | 0.538 | 0.000 | 0 | X | 0.000 | 0 | X | 0.000 | 0 | X |
| HumanPseudo5 | 446.425 | 3 | 2.909 | 138.000 | 1 | 0.901 | 142.500 | 1 | 1.046 | 131.000 | 1 | 0.689 |
| HFugu2r | 322.784 | 2 | 2.523 | 0.000 | 0 | X | 0.000 | 0 | X | 0.000 | 0 | X |
| HFortho1 | 282.933 | 2 | 1.381 | 0.000 | 0 | X | 0.000 | 0 | X | 0.000 | 0 | X |
| HFortho2 | 452.657 | 2 | 6.158 | 234.600 | 1 | 3.808 | 215.667 | 1 | 3.182 | 0.000 | 0 | X |
| HFortho3 | 627.357 | 4 | 3.894 | 0.000 | 0 | X | 0.000 | 0 | X | 0.000 | 0 | X |
| HFortho4 | 737.478 | 4 | 6.071 | 0.000 | 0 | X | 0.000 | 0 | X | 0.000 | 0 | X |
| HFortho5 | 217.274 | 1 | 3.328 | 0.000 | 0 | X | 0.000 | 0 | X | 0.000 | 0 | X |

TABLE 4

Unrelated Run Scores for PLAINS, EMBOSS, LAGAN, and LALIGN.

| Test Name | PLAINS | | | EMBOSS | | | LAGAN | | | LALIGN | | |
|---|---|---|---|---|---|---|---|---|---|---|---|---|
| | R | r | ζ' | R | r | ζ' | R | r | ζ' | R | r | ζ' |
| HFncd1 | 0.000 | 0 | X | 0.000 | 0 | X | 0.000 | 0 | X | 0.000 | 0 | X |
| HFncd2 | 0.000 | 0 | X | X | X | X | 0.000 | 0 | X | 0.000 | 0 | X |
| HFncd3 | 0.000 | 0 | X | X | X | X | 0.000 | 0 | X | 0.000 | 0 | X |
| FFcd1 | 0.000 | 0 | X | 0.000 | 0 | X | 0.000 | 0 | X | 0.000 | 0 | X |
| HFcd1 | 0.000 | 0 | X | 0.000 | 0 | X | 0.000 | 0 | X | 0.000 | 0 | X |
| HHcd1 | 139.604 | 1 | 1.568 | 0.000 | 0 | X | 0.000 | 0 | X | 0.000 | 0 | X |
| HMcd1 | 341.872 | 2 | 3.517 | 0.000 | 0 | X | 0.000 | 0 | X | 0.000 | 0 | X |
| MFcd1 | 0.000 | 0 | X | 0.000 | 0 | X | 0.000 | 0 | X | 0.000 | 0 | X |
| MMcd1 | 0.000 | 0 | X | 0.000 | 0 | X | 0.000 | 0 | X | 0.000 | 0 | X |

The CD1 and HFncd experiments involved unrelated non-random sequences. The underlying unrelatedness was the reason why, for the most part, no correlation was obtained by the exemplary PLAINS, EMBOSS, LAGAN, and LALIGN procedures in any of these experiments. The exemplary PLAINS EMBOSS, LAGAN, and LALIGN procedures catch no correlations when given randomly generated DNA sequences of lengths up to 8000 bp. The correlations that the exemplary PLAINS procedure determined in the Human-Human and Human-Mouse CD1 experiments are protein codon homologies, most of which being a short segment of perfect matches located relatively close to each other. Although these runs were meant to determine how the exemplary PLAINS procedure behaves with unrelated sequences, the correlations the exemplary PLAINS procedure obtained were discovered to be important but had been previously ignored.

Hence, the results obtained using the exemplary PLAINS procedure show PLAINS' superiority over the other alignment tools to be significant.

In all of these alignments, except HFOrtho2, the exemplary PLAINS procedure has demonstrated as being the only tool that obtains significant matches. For HFortho2, PLAINS received the most reliable results, followed by the EMBOSS procedure, and then the LAGAN procedure. Here, not only is the ζ' value for the exemplary PLAINS procedure better than that of the EMBOSS procedure, but the exemplary PLAINS procedure also obtained more common exons between the two related genomic sequences. The exemplary PLAINS procedure can become a technique of choice for aligning several thousand nucleotide DNA sequences, and possibly also for identifying exons between two genomes as diverged as human and fugu. FIG. 3 shows additional details of the results discussed herein above.

Each run of the exemplary PLAINS procedure to optimize gap/mismatch parameters on a pair of species took 30 minutes to 2 hours. The relatively long time taken by the exemplary PLAINS procedure is due to its preference for computing several hundred alignments under various gap/mismatch parameters before deciding which gap/mismatch parameters are the most optimal. For example, when ran using fixed-set gap-mismatch parameters, the exemplary PLAINS procedure ran in just under a minute, a constant factor of at most 5.6 times slower than the EMBOSS procedure. The reason for this slowdown is, e.g.: (1) the exemplary PLAINS procedure uses a linear space table instead of the quadratic space typical of dynamic programming, and (2) there is constant extra overhead in using Linked-List Assistance (mentioned earlier) to help create an alignment.

The exemplary implementation of PLAINS procedure can easily align a pair of sequences, each with nucleotides of up to 8 Kb. It can (1) attempt to obtain the best gap-mismatch parameters for a given pair of sequences and align with those parameters, or (2) use a user-specified set of gap-match parameters to align the pair of sequences. In (1), the runtime typically can range from 30 minutes to 2 hours. In (2), the runtime can typically range from 10 seconds to 1 minute. The exemplary PLAINS procedure can either be used via command line, or as part of the Valis tool set. More information can be found at http://bioinformatics.nyu.edu/~gill, the entire disclosure of which is incorporated herein by reference.

CONCLUSIONS AND FURTHER EMBODIMENTS

The exemplary PLAINS procedure is capable of obtaining more important correlations than other conventional procedures, e.g., in sequences of distant relation like Human and Fugu. The exemplary PLAINS procedure is also capable of distinguishing unimportant regions from important ones (since the exemplary PLAINS procedure does not need to obtain regions for randomly generated DNA sequences, and DNA sequences from Human/Mouse/Fugu with no protein codon homologies). Thus, the results yielded by the exemplary PLAINS procedure are preferable.

It is preferable for the exemplary PLAINS procedure to be run over sequences with more than 8000 nucleotides. The exemplary embodiment of the exemplary PLAINS procedure can perform localized alignment (since it generally discards leftmost and rightmost nucleotides that would be aligned against gaps), and therefore, in certain exemplary embodiments, it may be used for sequences of up to 8000 nucleotides.

Other exemplary embodiments contemplated herein include scaling the exemplary PLAINS procedure to search large sequences (of mega bases of nucleotides) for smaller areas where localized alignments can be performed, and then combining localized alignments to globalized alignments. The exemplary PLAINS procedure can become the preferable technique for aligning EST sequences to a genome.

Another exemplary embodiment contemplated herein involves adding a model to learn expected alignments over various species, as opposed to just merely approximating the best gap/mismatch parameters.

Still another exemplary embodiment contemplated herein includes a development of better statistics taking into account the base-pair compositions of the sequences (e.g., Nucleotide-bias, CG content, dinucleotides distribution, codon bias, etc.). The exemplary PLAINS procedure can assign a score of 1 to, e.g., a perfect match, and a score of ms (specified by user) to any mismatch. It may be useful to have a scoring matrix to assign different scores to different types of matches/mismatches. For example, if aligning a C against a T is more common than aligning at C against a G, then one can penalize the C-T mismatch less than the C-G mismatch when performing an alignment, etc.

APPENDIX

A Names of the Sequences Used

Tables 5 and 6 list exemplary specific sequences used in the experiments ran on PLAINS, EMBOSS, LAGAN, and LALIGN procedure.

TABLE 5

Sequence Details for the Related Experiments Ran. All the sequences are retrieved from ENSEMBL database [www.ensembl.org].

| Name | First Sequence | Second Sequence |
| --- | --- | --- |
| humanHomo1_15 | ENST00000263253 | ENSMUST00000050968 |
| humanHomo1_16 | ENST00000263253 | ENSMUST00000068387 |
| MousePseudo1 | ENSMUSG00000016720 | pseudogene |
| MousePseudo2 | ENSMUSG00000004038 | pseudogene |
| MousePseudo3 | ENSMUSG00000034321 | pseudogene |
| HumanPseudo1 | ENSG00000087086 | pseudogene |
| HumanPseudo2 | ENSG00000164104 | pseudogene |
| HumanPseudo3 | ENSG00000079432 | pseudogene |
| HumanPseudo4 | ENSG00000135486 | pseudogene |
| HumanPseudo5 | ENSG00000101210 | pseudogene |
| HFugu2r | ENSG00000111845 | SINFRUG00000137119 (reverse-complement) |
| HFortho1 | ENSG00000183628 | SINFRUG00000128815 |
| HFortho2 | ENSG00000099937 | SINFRUG00000140660 |
| HFortho3 | ENSG00000142168 | SINFRUG00000132716 |
| HFortho4 | ENSG00000138764 | SINFRUG00000152968 |
| HFortho5 | ENSG00000057757 | SINFRUG00000123004 |

TABLE 6

Sequence Details for the Unrelated Experiments Ran. All the sequences are retrieved from ENSEMBL database [www.ensembl.org].

| Name | First Sequence | Second Sequence |
| --- | --- | --- |
| HFncd1 | Human NCBI34:1:190164774:190174772 | FUGU2:scaffold_5343:1:5999:1 |
| HFncd2 | Human NCBI34:22:32724006:32744004:1 | FUGU2:scaffold_3421:1:9999:1 |
| HFncd3 | Human NCBI34:10:56721585:56731583:1 | FUGU2:scaffold_1415:1:6999:1 |
| FFcd1 | SINFRUT00000127255 | SINFRUT00000165154 |
| HFcd1 | ENSG00000150967.3 | SINFRUT00000127255 |
| HHcd1 | ENSG00000150967.3 | ENST00000259748 |
| HMcd1 | ENSG00000150967.3 | ENSMUST00000025930 |
| MFcd1 | ENSMUST00000025930 | SINFRUT00000165154 |
| MMcd1 | ENSMUST00000031354 | ENSMUST00000024034 |

B How Plains Generates an Alignment

As described herein, two strings to be aligned are denoted X and Y, and their respective lengths are m and n, and the penalty for each mismatch is denoted as ms.

The p-part piecewise-linear function ww(•), where, for some value i such that $k_{p-1} < i \leq k_p$, ww(i) is defined as:

$$ww(i) = wo + [wc_p(i - k_{p-1})] + \sum_{u=1}^{p-1} [wc_u(k_u - k_{u-1})].$$

Note that, for any i from 1 to m, a simple hash table can be helpful in determining in O(1) time which line of the piecewise-linear curves that an x-value of i is at. Since the length of a gap is at most m, it is not necessary to determine ww(i) for any i larger than m. This step, combined with explicitly saving to memory ww($k_u$) for all u from 0 to p−1, it is possible to determine ww(i) for any given i from 1 up to m in O(1) time.

Using a given p-part piecewise-linear gap function ww(•) and mismatch penalty ms, the exemplary PLAINS procedure can generate an alignment for X and Y of lengths m and n by maximizing V(m, n), where V(•,•) is a two-dimensional scoring function such that V(i, j) denotes, e.g., the best score for aligning X[1 . . . i] with Y[1 . . . j]. To assist in the computation of V(•,•), it is possible to use functions E(•,•), F(•,•), and G(•,•), where E(i, j) is the score for aligning X[1 . . . i] with Y[1 . . . j] when the "solid" character is obtained at the end of Y's suffix aligned against a gap, F(i, j) is the score for aligning X[1 . . . i] against Y[1 . . . j], when the "solid" character is obtained at the end of X's suffix aligned against a gap, and G(i, j) is the score for aligning X[1 . . . i] against Y[1 . . . j] when one ends with the "solid" characters at the end of the suffixes of X and Y aligned against each other (and they can be matched or mismatched). Because a simple alignment of DNA sequences is being considered, it is possible to assume s(c, d) gives a score of 1 when c=d, and score of −ms when c≠d. With all of this, dynamic programming scoring model for an alignment that may be used by the exemplary PLAINS procedure is:

$$V(0, 0) = 0;$$

$$V(i, 0) = E(i, 0) = -ww(i),$$

$$V(0, j) = F(0, j) = -ww(j);$$

$$V(i, j) = \max\{E(i, j), F(i, j), G(i, j)\},$$

$$G(i, j) = V(i-1, j-1) + s(X[i], Y[j]),$$

$$E(i, j) = \max_{0 \leq k \leq j-1} V[(i, k) - ww(j - k)],$$

$$F(i, j) = \max_{0 \leq k \leq i-1} V[(k, j) - ww(i - k)].$$

If p, the number of lines used in the ww(•) function is set to 1, the scoring model described above resembles a Smith-Waterman procedure, except that the Smith-Waterman procedure modifies E(•,•) and F(•,•) to improve runtime specifically for the case of affine gap functions. If p is set to m, then the scoring model mentioned above resembles Needleman-Wunsch.

B.1 Linked-List Assistance

The exemplary PLAINS procedure uses a Linked-List Assistance technique with many differences from that of those described in Miller, W. et al., "Sequence Comparison with Concave Weighting Functions", *Bulletin of Mathematical Biology*, 50:97-120, 1988. This technique involves considering possible solutions for the E(•,•) and F(•,•) entries before they are explicitly determined. To gain an intuition into this technique, j can be fixed in order to keep the discussion simple for the moment. Next, let eval(k,i)=V(k)−ww(i−k), and let $cand_k$(i) denote the k' value, where k'≦k, such that eval(k', i) is maximized, and let cand(i) denote the k' value, where k'<i, such that eval(k', i) is maximized. (Note that $cand_{i-1}$(i)=cand(i).)

Then, on the i'th iteration, with i'<i, with the knowledge of what V(i') is, one can simply take k'=$cand_{i-1}$(i'), and compare eval(k', i) with eval(i', i), and whichever of these two values is greater dictates $cand_{i'}$(i). When i'=i−1, this gives us cand(i), and thus on the ith iteration, F(i) (and subsequently V(i)) is known in O(1) time without the need to look backwards at previous V(•) entries. Next, it should be noted that:

(S1) If by the kth iteration of the procedure, it is known that, for some a, b, q and for all i' in [a, b], q=$cand_k$(i'). Then one can represent this fact with one data structure, instead of b−a+1 of them.

(S2) In all practical cases, the gap function ww is convex (meaning that ww(i) increases as i gets larger, but the rate of increase itself decreases as i gets larger). In this situation, it is known that if for some i'>i,eval(i,i')<eval(cand(i'),i'), then for all i">i, one also knows that eval(i,i")<eval(cand(i"),i"). Therefore, if at the end of the ith iteration, if the $cand_i$(•) values are scanned in the order: $cand_i$(i+1), $cand_i$(i+2), . . . , $cand_i$(m), then the $cand_i$(•) entries would be seen as non-increasing (each next $cand_i$(•) entry is either smaller or equal to the previous one).

Thus, it is possible to determine and collect adjacent indices with the same $cand_i$(•) values into a single group. One element can be maintained per group in a data structure. Each group can be represented by a single element. This element can contain the winner=$cand_i$(•) value for all indices represented by the group, as well the value v=V(winner), and the leftmost and rightmost indices of the group, lwb and upb. The elements can be listed in order from leftmost to rightmost indices in this list L. It is preferable to add or delete elements from L to correspond to groups being split off or merged when one goes from the ith iteration to the (i+1) th iteration. See example below:

Furthermore, from (S2), it is known that on the ith iteration, if $cand_i$(i+1)≠i, then for all i'>i, $cand_i$(i')≠i. If there exists an a such that for all ĩ such that i+1≦ĩ≦a, $cand_i$(ĩ)=i, and $cand_i$(a+1)≠i then for all i'>a, $cand_i$(i')≠i. Hence, on the ith iteration, it is possible to proceed on the elements of L from left to right to find the rightmost value a such that $cand_i$(a)=i, delete any element of previous winner entries, and add in a single leftmost element to L with i as its winner, and lwb and upb set accordingly.

In the case that on the ith iteration, there is an element in L such that $cand_i$(lwb)=i, but $cand_i$(upb)≠i, and its index within the group is the largest a value such that $cand_i$(a)=i, then, the element's previous winner value of k can be taken, its v value, and consider for x the plots of v−ww(x−k) versus V(i)−ww(x−i). One seeks the point where the first plot intersects the second one. The two plots involve p-part piecewise-linear curves, and binary search over the lines of these curves (which takes O(log p) time) determines which lines on these curves contain the intersection. At this point, one can get the intersection point itself in O(1) time. From this process, it is possible to determine the largest a such that $\text{cand}_i(a)=i$, with $\text{lwb} \leq a \leq \text{ubp}$, and then update the elements of L accordingly.

This procedure can use list L to obtain solutions for F(•) in O(m log p) time. At any time, the exemplary PLAINS procedure has O(p) elements in L (and p<<m typically). In Appendix D is presented a proof showing that the main procedure differs from the Miller-Myers method in achieving the O(p) worst-case space complexity in L For now, assume that one were to return to the two-dimensional computational model, but use it in the manner outlined here. The exemplary PLAINS procedure determines entries to the V, E, F, and G tables column by column. For each row j, it is possible to determine F(•,j) with the assistance of a list $L_j$ (such as lists $L_0, L_1, \ldots, L_n$ are maintained, and each list is updated in the manner explained earlier), and for each column i, it is possible to determine E(i, •) using the list R (which can be updated in a manner similar to that of L for the F entries, except that when a determination column of the table is completed, R can be emptied so it can be reused when proceeding to the next column). The updates for R and each $L_j$ list can be interweaved. This implies O(mn log p) time complexity, and further implies that all lists combined take up O(np) space, assuming each list uses O(p) space.

See Appendix sections C and D for a discussion of how the exemplary PLAINS procedure may use O(n) space from the V(•,•), E(•,•), F(•,•), and G(•,•) tables, and a proof of correctness for the scheme used.

C Table Space Reduction

The exemplary PLAINS procedure can use only O(n) space for its dynamic programming tables V, E, F, and G because it exploits a method, generalizing several concepts described in Hirschberg, and later Miller-Meyers publications provided in Miller, W. et al., "Optimal Alignments in Linear Space", *CABIOS*, 4:11-17, 1988. This space-optimal approach, in addition to using X and Y to determine tables V, E, F, and G, also can use $X^r$ and $Y^r$ (the reversed strings of X and Y) to compute tables $X^r$, $G^r$, $E^r$, and $F^r$. Here, $V^r(i,j)$ denotes the score for the first i entries of $X^r$ and the first j entries of $Y^r$—in other words, the last i entries of X and the last j entries of Y. And, $E^r(i,j)$, $F^r(i,j)$, and $G^r(i,j)$, behave similar to E(i,j), F(i,j), and G(i,j), over the first i entries of $X^r$ and the first j entries of $Y^r$. The lists $L^r_j$ are maintained to assist in computing $F^r(•,j)$, and list $R^r$ to assist in computing each ith column of $E^r(i,•)$ in a manner similar to the way $L_j$ was used for F(•,j) and R for E(i,•). The exemplary PLAINS procedure can save the t most recently computed columns of V, E, F, G, $V^r$, $E^r$, $F^r$, and $G^r$, where t is some fixed constant. It is possible to correctly maintain the $L_j$, $L^r_j$, R and $R^r$ lists, and determine all table entries, while only saving the t most recent columns, since any earlier important V and $V^r$ values that are relevant are already saved in the lists.

In this manner, by determining V, E, F, G for X[1 ... m/2] and Y[1 ... n], and $V^r$, $E^r$, $F^r$, $G^r$ for $X^r[1 \ldots m/2]$ and $Y^r[1 \ldots n]$ (which are really X[(m/2)+1 ... m] and Y[1 ... n]), the exemplary PLAINS procedure can use a "maximum criteria" described herein to obtain a "middle" subalignment from the saved portions of V, E, F, G, and $V^r$, $E^r$, $F^r$, $G^r$. With this "middle" subalignment known, and similar to Hirschberg's procedure the exemplary PLAINS procedure makes two recursions, one to obtain a sub-alignment for the left characters of X and Y, and another to obtain a subalignment for the right characters of X and Y. All of these subalignments are glued together to get the overall alignment for X and Y.

This exemplary method of using O(n) space for the tables to get an alignment can increase overall runtime by at most a constant factor compared to the intuitive O(mn) space method of saving all columns of all tables. Hence, the overall runtime for the exemplary PLAINS procedure in creating an alignment is O(mn log p).

To explain the "maximum criteria" selection, let $\text{cand}_k^L(i,j)$ denote the $\text{cand}_k(i)$ derived from list $L_j$, and let $\text{eval}_j(k,i)$ denote V(k,j)−ww(i−k) (e.g., $\text{eval}_j(k,i)$ is the two-dimensional version of eval(k,i)). And let gr(k) denote V(m/2,k)+ $V^r$(m/2,n−k). Also, let er(k,k') denote $V^r$(m−k',n−k)+$\text{eval}_k$ $(\text{cand}_{m/2}^L(k',k),k')$.

When p is 1, $V(m,n)=\max_k[gr(k)]$, as described by the Hirschberg procedure. Therefore, when p=1, it is satisfactory to select the "maximum criteria" to select a k such that gr(k) is maximized, then use V(m/2,k) and $V^r$(m/2,n−k) to obtain two subalignments from the saved columns of V and $V^r$ based on this. These subalignments are attached together to make a "middle" subalignment (and this is approximately the subalignment that uses middle bits of X).

When p>1, each $L_j$ list can be determined assuming the indices i can range from 0 to m, not 0 to m/2 (even though that may be all one needs for the V table). Then, by the end of computing the V table, it is possible to use $L_j$ while determining the $V^r$ table and $L^r$ lists to obtain rc(j) values for each j, denoting an endpoint for X against a gap that uses row j of the tables. If er(k, k') denote $V^r$(m−k', n−k)+$\text{eval}_k(\text{cand}_{m/2}^L(k',k)$, k'), then the "maximum criteria" becomes to select a k that maximizes $$k^* = \operatorname*{argmax}_k \{gr(k),\ er(k,\ rc(k))\}.$$

While determining $V^r$, entries can be read from $L_j$, without making any changes thereto. Formally, rc(j) is the i value in range [m/2, m] such that er(j, i) is maximized. A deeper intuition for rc(j) is described in the next section.

For the selected k, in the event that er(k) is larger, then the optimal alignment uses X against a gap are known, with this gap starting in the first half of X and ending in the second half of X, and one has $\text{cand}_{m/2}^L(\text{rc}(k),k)$ and rc(k) as the right and left endpoints to this gap. This can be used to construct a subalignment with this gap, and use whatever can be saved of V and $V^r$ to obtain any additional subalignment parts for characters left and right of this gap. Therefore, the "middle" subalignment is obtained.

Similarly, for the selected k, in the event that gr(k) is larger, then one knows the optimal alignment does not involve X against a gap is known, with this gap starting in the first half of X and ending in the second half of X. Therefore, it is possible to trace the subalignments from the appropriate points in the V and $V^r$ tables the same way one would for the p=1 case to get the "middle" subalignment.

The proof of correctness for the selection of k in this manner is described in the next section.

D Proofs to the Nontrivial Portions of Procedure

In generating an alignment from a given set of parameters, there are two features the exemplary PLAINS procedure has that make it stand out. First, the exemplary PLAINS procedure uses O(np) space in the worst-case scenario. Second, under its given space and runtime bounds, the exemplary PLAINS procedure obtains the correct alignment based on the given piecewise-linear function ww(•).

These two features of the exemplary PLAINS procedure are nontrivial and tedious. For the second of these two features, proving the correctness of alignment obtained by the exemplary PLAINS procedure includes proving the correctness of the "maximum criteria" selection employed by PLAINS procedure when using V and V$^r$ tables to assist in generating the alignment. The following description provides exemplary proofs of the procedure.

D.1 Proof for O(np) Space Bound, Plains Procedure

As described above, the exemplary PLAINS procedure uses an O(np) space worst-case when using p-part piecewise-linear function ww(•) (and when p<<m, as is in the exemplary PLAINS procedure, then this can result in a substantial improvement over the quadratic space complexity). This, in fact, is the main innovation of the exemplary PLAINS procedure over the original intuitions of the Miller-Myers procedure.

As described above, the exemplary PLAINS procedure can use O(n) space from the tables because it may saves the t most recently computed columns of all tables, and uses recursion to obtain unknown portions of the alignment. The space taken up by the recursions is O(log m), however in practice, m and n can be assumed to differ from each other by a constant factor, and hence the O(log m) space used by recursion may be less than the O(n) space used by the tables.

What generally uses the most space in the exemplary PLAINS procedure is not the tables, but the lists of form $L_j$, $L^r_j$, R R$^r$ used to compute the tables. The following description proves that each list used in the exemplary PLAINS procedure uses O(p) space.

Assuming for simplicity that j is fixed so that one is dealing for all i with V(i) and F(i), and linked-list L can be used to obtain the much-needed solutions for F and V. (I.e., V(i)=V(i, j) and F(i)=F(i, j) and L is how one gets values for V and F.)

CLAIM: For p-part function ww(•), L will always have at most p elements in it.

PROOF: In the beginning, when i=0, L starts with one element. Thereafter, in some ith iteration, after one iteration completed computing V(i), if an element of L is split with winner k and value v (where v=V(k)), then this implies that, for some x, the $k_{th}$ plot of v−ww(x−k) intersects the $i_{th}$ plot of V(i)−ww(x−i) (i.e., V(i)−ww(x−i)=v−ww(x−k) for some x). However, both of these plots are identical in shape. By translating one horizontally and vertically, this plot can fit perfectly into the other.

Therefore, in considering the lines from both plots that intersect (assuming $p_1$th line from the $i_{th}$ plot and the $p_2$th line from the k$^{th}$ plot intersect), since k<i, the $p_1$th line from the $i_{th}$ plot must have a higher downward slope than that of the $p_2$th line from the $k_{th}$ plot. Therefore $p_1<p_2$. (So, a given line from the $i_{th}$ plot intersects a later line from the $k_{th}$ plot.)

Hence, if list L has p elements, this implies having found p−1 intersections, each from a different plot. This can mean that cand(•) values taken from the $ur_1$th line of some $q_1$ plot intersecting the $ul_2$th line of some $q_2$ plot, and the $ur_2$th line of the $q_2$ plot intersects the $ul_3$th line of the $q_3$ plot, and so on up to the $q_p$ plot may be obtained, and therefore:

$$ur_1 < ul_2 \leq ur_2 < ul_3 \leq ur_3 \ldots ur_{p-1} < ul_p.$$

However, all of these plots may likely have exactly p lines. Therefore, in this case, for each h from 1 to p, $ul_h=ur_h$ should be true. Hence for all h from 1 to p, the $ul_h$ values correspond to all the lines of the ww function (meaning $ul_h$=h for all h).

In this case, for each element g in L, if g uses the $q_h$ plot for some value h, then likely only one line from the $q_h$ plot, the $ul_h$th line, can provide the best solution for indices from the $[g_l,g_r]$ interval ($g_l$ and $g_r$ are the lwb and upb values for element g in list L).

Therefore, if during the ith iteration, p elements in L are provided, then the i plot of V(i)−ww(x−i) will have lines of the same slopes as those corresponding to lines $ul_1$ through $ul_p$. Therefore, if the p'th-line of the $i_{th}$ plot intersects some $q_{h'}$ plot (with h'≧2), then all elements of L derived from $q_{h'}$ plots with $ul_{h'} \leq p'$ may possibly be discarded (i.e., at least one element of L will definitely get discarded, and one new element with i as its cand(•) value is created, implying that total number of elements in L overall in this $i_{th}$ iteration will either remain the same or decrease). It is likely impossible for the i-curve's p'th-line to intersect the $q_1$ plot.

Thus, it is likely never possible to increase the number of elements in L from p to p+1. So L always has O(p) elements in it.

Therefore, in returning to the 2-dimensional model, the n different linked lists of form $L_j$ and $L^r_j$ each use O(p) space, and similarly, R and R$^r$ also each use O(p) space. Hence, the total space used by all of the lists is O(np).

D.2 Definition of rc(j)

Before the discussion of the next section, where the correctness of the "maximum criteria" selection rule used by the exemplary PLAINS procedure is described, it may be helpful to define rc(j).

Suppose that one fixes the index j used by the procedure in the V and V$^r$ tables so that it flattens to one dimension in order to keep the arguments simple. Then, assume V(i)=V(i, j), F(i)=F(i, j), V$^r$(i)=V$^r$(i, n−j), and F$^r$(i)=F$^r$(i, n−j). Thus, the most recently found t entries from V and V$^r$ can be stored, where t is some constant at least 1. Saving the t most recently-computed entries for V(•) and V$^r$(•) can correspond to saving the t most recently computed columns of V(•,•) and V$^r$(•,•) in the two-dimensional model.

During the computations of V and V$^r$, a linked list L can be used to maintain solutions for F, and a linked list L$^r$ to maintain solutions for F$^r$. Next, assume that all of the F and V entries are computed before starting on the F$^r$ and V$^r$ entries, and L is reviewed while computing V$^r$ (but one does not modify L while computing V$^r$).

Suppose also that while computing V, list L maintains cand(i) for all i from 0 to m, (even though one only need indices of i from 0 through m/2 to complete computations for F and V), and therefore, when the determination of V and L is completed, list L now has the $cand_{m/2}$(i) values for all i from m/2 to m. Hence, after computing F and V, it is know that:

For any i in range [(m/2)+1, m]: If i=$cand_{m/2}$(i), then i is the number in range [0, m/2] such that V(i')−ww(i'−i) is maximized.

During the process of computing the V$^r$ entries, one possible best alignment solution in combining both the V and V$^r$ tables could be V(i')−ww(i'−i)+V$^r$(m−i) (a solution with a gap starting in the first half of X and ending in the second half of X).

Suppose there is some extra variable rc equal to the i in range [(m/2)+1, m] such that V($cand_{m/2}$(i))−ww(i−$cand_{m/2}$(i))+V$^r$(m−i)=eval($cand_{m/2}$(i),i)+V$^r$[m−i] is maximized. It is possible to determine the value for rc while computing the entries for V$^r$ using the list L. In considering all possible alignments that have a gap starting in the first half of X and ending in the second half of X, one knows that rc and $\text{cand}_{m/2}(\text{rc})$ gives the coordinates in the right and left halves of X of the gap for the best-scoring alignment of this type.

Switching over to using all rows in computing the F, V, $F^r$, and $V^r$ tables, it is possible to have, for each row j from 0 to n, a value rc(j) which is equal to the i in range [(m/2)+1, m] such that $V(\text{cand}_{m/2}^L(i,j),j) - ww(i - \text{cand}_{m/2}^L(i,j)) + V^r(m-i,n-j) = \text{eval}_j(\text{cand}_{m/2}^L(i,j),i) + V^r(m-i,n-j) = er(j,i)$ is maximized.

D.3 Proof of Correctness in "Maximum Criteria" Selection

As described above, in the exemplary PLAINS procedure's determination of the V and $V^r$ tables, the "maximum criteria" selection is used to find a k that maximizes max{gr(k), er(k, rc(k))}. Below is a proof for the correctness of this procedure.

In the alignment of X against Y, two general cases may occur.
1. X may be provided which is aligned against a gap of a type starting in the first half of X, and ending in the second half of X.
2. X may be provided which is aligned against a gap of a type starting in the first half of X, and ending in the second half of X.

When case (2) occurs, (which is what the V and $V^r$ tables do), it is possible to align X[1 ... m/2] against Y separately from aligning X[m/2 ... m] against Y. Furthermore, there exists a k' such that for all i and i' and j, $V(m/2, k') + V^r(m/2, n-k') > V(i,j) + V^r(m-i', n-j) - ww(i'-i)$. Therefore for this k' value, $gr(k') > er(k', rc(k'))$.

Thus, it is possible to obtain the correct alignment by selecting a k that maximizes gr(k). Therefore, selecting a k such that max{gr(k), er(k, rc(k))} is maximized gives the correct alignment in this case.

When case (1) occurs, then there exists an i, i', and j such that for all k', $V(i, j) + V^r(m-i', n-j) - ww(i'-i) > V(m/2, k') + V^r(m/2, n-k')$. Furthermore, for a fixed pair of i' and j, note that $i = \text{cand}_{m/2}^L(i',j)$, the $\text{cand}_{m/2}(i')$ value from the $L_j$ list, maximizes $V(i,j) + V^r(m-i', n-j) - ww(i'-i)$. Next, note that if j is fixed, setting i'=rc(j) and hence $i = \text{cand}_{m/2}^L(i',j)$ maximizes $V(i, j) + V^r(m-i', n-j) - ww(i'-i) = V(\text{cand}_{m/2}^L(i',j),j) - ww(i' - \text{cand}_{m/2}^L(i',j)) + V^r(m-i', n-j) = \text{eval}_j(\text{cand}_{m/2}^L(i',j),i') + V^r(m-i', n-j) = er(j, i')$. Therefore, one obtains the highest scoring alignment by selecting a k' that maximizes er(k', rc(k')). Therefore, by selecting a k that maximizes max{gr(k), er(k, rc(k))}, the algorithm computes the correct alignment in this case.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced or listed herein are incorporated herein by reference in their entireties.

What is claimed is:

1. A process for obtaining data associated with an alignment between at least two data strings having a plurality of positions in the data strings, comprising:

using a computer, automatically determining at least one characteristic of an alignment between the data strings using a particular function, the particular function facilitating an evaluation of gaps between the strings in the alignment based on a piecewise-linear non-affine gap-penalty function, wherein the gap-penalty function is a piecewise-linear function defined by:

$$ww(i) = wo + [wc_p(i - k_{p-1})] + \sum_{u=1}^{p-1} [wc_u(k_u - k_{u-1})]$$

wherein i is a value such that $k_{p-1} < i \leq k_p$, ww(i), wherein the function has a y-intercept of wo, and slopes of linear functions in successive intervals are $wc_1, wc_2, \ldots, wc_p$, wherein the x-values at which one of the intervals ends and a next of the intervals begins are denoted $k_1, k_2, \ldots, k_{p-1}$, wherein $k_u$ is the x-value where the $u_{th}$ linear function of slope $wc_u$ ends, where $k_0 = 0$, and wherein $p_{th}$ function of slope $wc_p$ extends off into infinity;

determining the alignment with a computation time that is proportional to products of lengths of the data strings, the alignment being determined using space that is proportional to a sum of the lengths of the data strings; and at least one of displaying or storing the data in a storage arrangement in at least one of a user-accessible format or a user-readable format.

2. The method of claim 1, wherein each of the data strings represents a nucleic acid sequence.

3. The method of claim 1, wherein each of the data strings represents a protein sequence.

4. The method of claim 1, further comprising automatically optimizing a set of gap/match-mismatch parameters $\alpha$, $\beta$, d, and ms as a function of the gaps, wherein $\alpha$ is a log base, $\beta$ is a y-intercept, d is the piecewise-linear function, and wherein ms is a penalty for each mismatch in the alignment.

5. The method of claim 4, wherein the piecewise-linear function approximates a logarithmic gap penalty function over i is denoted as: $\alpha \ln(i+1) + \beta$, where for a given d, $\alpha$, and $\beta$, ww(•) uses $k_1, \ldots, k_p$ values set to d, 2d, ..., p*d, wherein, for each u from 0 to p, $ww(ku) = \alpha \log(ku+1) + \beta$ that is used to calculate a slope wcu for each uth line, and wherein wo is set to $\beta$.

6. The method of claim 4, wherein the segment pairs are selected according to the following substeps:

(a) for all i from 1 to a−(W−1), computing a pa(i) value, which is the percentage of entries in A[i ... i+W−1], where a match has occurred, and computing $\mu$ and $\sigma$, the mean and standard deviation of the pa(•) values, marking any pa(•) values as "special" if they exceed $\mu + \omega\sigma$;

(b) for each u and u' (with u<=u'), if pa(u), pa(u+1), ... pa(u'), if all marked as in a particular manner, and pa(u−1) and pa(u'+1) are not marked in the particular manner, then generating a segment pair that starts at the leftmost entry pa(u) represents, and ends at the rightmost entry that pa(u') represents, defined by the range A[u ... u'+W−1];

(c) reducing each segment pair P so that it starts and ends at a position in the alignment where a match occurred, and merging any segment pairs that overlap, wherein if a segment pair $P_1$ starts at position $u_1$ and ends at position $v_1$, and a segment pair $P_2$ starts at position $u_2$ and ends at position $v_2$, and $u_1 < u_2$, and $v_1 \geq u_2$, one merges the two segment pairs into a new segment pair P which begins at $u_1$ and ends at max($v_1, v_2$));

(d) providing a score S to all segment pairs representing non-overlapping regions, wherein if a segment pair P starts at position u and ends at position v, then a score of subalignment A[u . . . v] is calculated using the given gap/mismatch penalties ww and ms and wherein each match is given 1 point per match;

(e) for each score S given to each segment pair P, determining a Karlin-Atschul probability p=1−exp(−Kmne$^{-\lambda S}$), and deleting any segment pairs whose p>ρ to define a set of segment pairs r, and (f) determining R for the set of kept segment pairs, where R is a sum of the scores of the kept segment pairs, and wherein if the ith kept segment pair has score $S_i$, then $$\left(R = \sum_{i=1}^{r} [S_i]\right).$$

7. The method of claim 1, wherein the particular function is a score function.

8. The method of claim 1, wherein the at least one characteristic includes a goodness characteristic of an alignment between the data strings.

9. The method of claim 1, wherein the gaps are evaluated based on a function that is at least one of modeled and approximated based on the non-affine function.

10. The method of claim 1, further comprising determining a best alignment by scoring a selection of segment pairs.

11. The method of claim 1, further comprising determining a best alignment using dynamic programming recurrence relations.

12. A software arrangement, stored on a non-transitory computer-readable medium, for obtaining data associated with an alignment between at least two data strings having a plurality of positions in the data strings, comprising:
a set of instructions, which when executed by a computer, configure the computer to:
determine at least one characteristic of an alignment between the data strings using a particular function, the particular function facilitating the evaluation of gaps between the strings in the alignment based on a piecewise-linear non-affine gap-penalty function, wherein the gap-penalty function is a piecewise-linear function defined by:

$$ww(i) = wo + [wc_{\bar{p}}(i - k_{\bar{p}-1})] + \sum_{u=1}^{\bar{p}-1} [wc_u(k_u - k_{u-1})]$$

wherein i is a value such that $k_{p-1} < i \leq k_p$, ww(i), wherein the function has a y-intercept of wo, and slopes of linear functions in successive intervals are $wc_1, wc_2, \ldots, wc_p$, wherein the x-values at which one of the intervals ends and a next of the intervals begins are denoted $k_1, k_2, \ldots, k_{p-1}$, wherein $k_u$ is the x-value where the $u_{th}$ linear function of slope $wc_u$ ends, where $k_0=0$, and wherein $p_{th}$ function of slope $wc_p$ extends off into infinity;
determine the alignment with a computation time that is proportional to products of lengths of the strings, the alignment being determined using space that is proportional to a sum of the lengths of the data strings; and
at least one of display or store the data in a storage arrangement in at least one of a user-accessible format or a user-readable format.

13. A system for obtaining data associated with an alignment between at least two data strings having a plurality of positions in the data strings, comprising:
a computer which is configured to:
determine at least one characteristic of an alignment between the data strings using a particular function, the particular function facilitating the evaluation of gaps between the strings in the alignment based on a piecewise-linear non-affine gap-penalty function, wherein the gap-penalty function is a piecewise-linear function defined by:

$$ww(i) = wo + [wc_{\bar{p}}(i - k_{\bar{p}-1})] + \sum_{u=1}^{\bar{p}-1} [wc_u(k_u - k_{u-1})]$$

wherein i is a value such that $k_{p-1} < i \leq k_p$, ww(i), wherein the function has a y-intercept of wo, and slopes of linear functions in successive intervals are $wc_1, wc_2, \ldots, wc_p$, wherein the x-values at which one of the intervals ends and a next of the intervals begins are denoted $k_1, k_2, \ldots, k_{p-1}$, wherein $k_u$ is the x-value where the $u_{th}$ linear function of slope $wc_u$ ends, where $k_0=0$, and wherein $p_{th}$ function of slope $wc_p$ extends off into infinity;
determine the alignment with a computation time that is proportional to products of lengths of the strings, the alignment being determined using space that is proportional to a sum of the lengths of the data strings; and
at least one of display or store the data in a storage arrangement in at least one of a user-accessible format or a user-readable format.

14. The method of claim 1, further comprising selecting a set of parameters for use in the non-affine gap penalty function.

15. The method of claim 14, further comprising fixing the selected set of parameters so that a score function is constant.

16. The software arrangement of claim 12, wherein each of the data strings represents a nucleic acid sequence.

17. The software arrangement of claim 12, wherein each of the data strings represents a protein sequence.

18. The software arrangement of claim 12, further comprising automatically optimizing a set of gap/match-mismatch parameters α, β, d, and ms as a function of the gaps, wherein α is a log base, β is a y-intercept, d is the piecewise-linear function, and wherein ms is a penalty for each mismatch in the alignment.

19. The software arrangement of claim 18, wherein the piecewise-linear function approximates a logarithmic gap penalty function over i is denoted as: α ln(i+1)+β, where for a given d, α, and β, ww(•) uses $k_1, \ldots, k_p$ values set to d, 2d, . . . , p*d, wherein, for each u from 0 to p, ww(ku)=α log(ku+1)+β that is used to calculate a slope wcu for each uth line, and wherein wo is set to β.

20. The software arrangement of claim 18, wherein the segment pairs are selected according to the following substeps:

(a) for all i from 1 to a−(W−1), computing a pa(i) value, which is the percentage of entries in A[i . . . i+W−1], where a match has occurred, and computing μ and σ, the mean and standard deviation of the pa(•) values, marking any pa(•) values as "special" if they exceed μ+ωσ;

(b) for each u and u' (with u<=u'), if pa(u), pa(u+1), . . . pa(u'), if all marked as in a particular manner, and pa(u−1) and pa(u'+1) are not marked in the particular manner, then generating a segment pair that starts at the leftmost entry pa(u) represents, and ends at the rightmost entry that pa(u') represents, defined by the range A[u . . . u'+W−1];

(c) reducing each segment pair P so that it starts and ends at a position in the alignment where a match occurred, and merging any segment pairs that overlap, wherein if a segment pair $P_1$ starts at position $u_1$ and ends at position $v_1$, and a segment pair $P_2$ starts at position $u_2$ and ends at position $v_2$, and $u_1 < u_2$, and $v_1 \geq u_2$, one merges the two segment pairs into a new segment pair P which begins at $u_1$ and ends at $max(v_1, v_2)$);

(d) providing a score S to all segment pairs representing non-overlapping regions, wherein if a segment pair P starts at position u and ends at position v, then a score of subalignment A[u . . . v] is calculated using the given gap/mismatch penalties ww and ms and wherein each match is given 1 point per match;

(e) for each score S given to each segment pair P, determining a Karlin-Atschul probability $p=1-\exp(-Kmne^{-\lambda S})$, and deleting any segment pairs whose p>ρ to define a set of segment pairs r, and (f) determining R for the set of kept segment pairs, where R is a sum of the scores of the kept segment pairs, and wherein if the ith kept segment pair has score $S_i$, then $$\left(R = \sum_{i=1}^{r} [S_i]\right).$$

21. The software arrangement of claim 12, wherein the particular function is a score function.

22. The software arrangement of claim 12, wherein the at least one characteristic includes a goodness characteristic of an alignment between the data strings.

23. The software arrangement of claim 12, wherein the gaps are evaluated based on a function that is at least one of modeled and approximated based on the non-affine function.

24. The software arrangement of claim 12, further comprising determining the alignment which is approximately optimal in substantially all circumstance for a computation time that is proportional to products of lengths of the strings, the alignment being determined using space that is proportional to a sum of the lengths of the data strings.

25. The software arrangement of claim 12, further comprising determining a best alignment by scoring a selection of segment pairs.

26. The software arrangement of claim 12, further comprising determining a best alignment using dynamic programming recurrence relations.

27. The system of claim 13, wherein each of the data strings represents a nucleic acid sequence.

28. The system of claim 13, wherein each of the data strings represents a protein sequence.

29. The system of claim 13, further comprising automatically optimizing a set of gap/match-mismatch parameters α, β, d, and ms as a function of the gaps, wherein α is a log base, β is a y-intercept, d is the piecewise-linear function, and wherein ms is a penalty for each mismatch in the alignment.

30. The system of claim 29, wherein the piecewise-linear function approximates a logarithmic gap penalty function over i is denoted as: $\alpha \ln(i+1)+\beta$, where for a given d, α, and β, ww(•) uses $k_1, \ldots, k_p$ values set to d, 2d, . . . , p*d, wherein, for each u from 0 to p, $ww(ku)=\alpha \log(ku+1)+\beta$ that is used to calculate a slope wcu for each uth line, and wherein wo is set to β.

31. The system of claim 29, wherein the segment pairs are selected according to the following substeps:

(a) for all i from 1 to a−(W−1), computing a pa(i) value, which is the percentage of entries in A[i . . . i+W−1], where a match has occurred, and computing μ and σ, the mean and standard deviation of the pa(•) values, marking any pa(•) values as "special" if they exceed μ+ωσ;

(b) for each u and u' (with u<=u'), if pa(u), pa(u+1), . . . pa(u'), if all marked as in a particular manner, and pa(u−1) and pa(u'+1) are not marked in the particular manner, then generating a segment pair that starts at the leftmost entry pa(u) represents, and ends at the rightmost entry that pa(u') represents, defined by the range A[u . . . u'+W−1];

(c) reducing each segment pair P so that it starts and ends at a position in the alignment where a match occurred, and merging any segment pairs that overlap, wherein if a segment pair $P_1$ starts at position $u_1$ and ends at position $v_1$, and a segment pair $P_2$ starts at position $u_2$ and ends at position $v_2$, and $u_1 < u_2$, and $v_1 \geq u_2$, one merges the two segment pairs into a new segment pair P which begins at $u_1$ and ends at $max(v_1, v_2)$);

(d) providing a score S to all segment pairs representing non-overlapping regions, wherein if a segment pair P starts at position u and ends at position v, then a score of subalignment A[u . . . v] is calculated using the given gap/mismatch penalties ww and ms and wherein each match is given 1 point per match;

(e) for each score S given to each segment pair P, determining a Karlin-Atschul probability $p=1-\exp(-Kmne^{-\lambda S})$, and deleting any segment pairs whose p>ρ to define a set of segment pairs r, and (f) determining R for the set of kept segment pairs, where R is a sum of the scores of the kept segment pairs, and wherein if the ith kept segment pair has score $S_i$, then $$\left(R = \sum_{i=1}^{r} [S_i]\right).$$

32. The system of claim 13, wherein the particular function is a score function.

33. The system of claim 13, wherein the at least one characteristic includes a goodness characteristic of an alignment between the data strings.

34. The system of claim 13, wherein the gaps are evaluated based on a function that is at least one of modeled and approximated based on the non-affine function.

35. The system of claim 13, further comprising:
    determining the alignment which is approximately optimal in substantially all circumstance for a computation time that is proportional to products of lengths of the strings, the alignment being determined using space that is proportional to a sum of the lengths of the data strings.

36. The system of claim 13, further comprising determining a best alignment by scoring a selection of segment pairs.

37. The system of claim 13, further comprising determining a best alignment using dynamic programming recurrence relations.

38. The method of claim 1, wherein the computation time is proportional to the products of the lengths of the data strings and the log of the number of pieces in the piecewise linear function.

* * * * *